(12) United States Patent
Shen et al.

(10) Patent No.: US 8,609,842 B2
(45) Date of Patent: Dec. 17, 2013

(54) METHOD FOR SYNTHESIZING IMATINIB

(75) Inventors: Xin Shen, Shanghai (CN); Xiao He, Shanghai (CN); Jidong Yang, Shanghai (CN); Shaohong Wu, Kunming (CN); Huaxing Zhan, Shanghai (CN)

(73) Assignees: Fujian South Pharmaceutical Co., Ltd., Fujian (CN); Shanghai Parling Pharmatech Co., Ltd., Shanghai (CN)

( * ) Notice: Subject to any disclaimer, the term of this patent is extended or adjusted under 35 U.S.C. 154(b) by 0 days.

(21) Appl. No.: 12/866,776

(22) PCT Filed: Apr. 23, 2010

(86) PCT No.: PCT/CN2010/072112
§ 371 (c)(1),
(2), (4) Date: Aug. 9, 2010

(87) PCT Pub. No.: WO2011/130918
PCT Pub. Date: Oct. 27, 2011

(65) Prior Publication Data
US 2013/0041149 A1    Feb. 14, 2013

(51) Int. Cl.
*C07D 401/14* (2006.01)
(52) U.S. Cl.
USPC .......................... 544/331; 544/242; 544/330
(58) Field of Classification Search
USPC .......................... 544/242, 322, 331
See application file for complete search history.

(56) References Cited

U.S. PATENT DOCUMENTS

| | | | |
|---|---|---|---|
| 4,623,486 A | 11/1986 | Lombardino | |
| 7,151,106 B2 | 12/2006 | Hayry | |
| 7,579,467 B2 * | 8/2009 | Loiseleur et al. | 544/393 |
| 7,638,627 B2 * | 12/2009 | Kankan et al. | 544/331 |
| 2006/0135527 A1 | 6/2006 | Houghton et al. | |
| 2006/0142580 A1 | 6/2006 | Loiseleur et al. | |
| 2006/0173182 A1 | 8/2006 | Kankan et al. | |
| 2007/0197545 A1 | 8/2007 | Szczepek et al. | |
| 2007/0265288 A1 | 11/2007 | Pathi et al. | |
| 2007/0293683 A1 | 12/2007 | Loiseleur et al. | |
| 2008/0090833 A1 | 4/2008 | Jegorov et al. | |

FOREIGN PATENT DOCUMENTS

| WO | WO 2004-024895 | 3/2004 |
|---|---|---|
| WO | WO 2004-108699 | 12/2004 |
| WO | WO 2007-062142 | 5/2007 |

OTHER PUBLICATIONS

Potluri et al (2008): STN International HCAPLUS database, (Columbus, Ohio), Accession No. 2008: 1465920.*
The International Search Report of the International Searching Authority for PCT/CN2010/072112, date completed Dec. 25, 2010, date mailed Feb. 10, 2011.

* cited by examiner

*Primary Examiner* — Golam M M Shameem
(74) *Attorney, Agent, or Firm* — Weisun Rao; Greenberg Traurig, LLP

(57) ABSTRACT

In the present invention, a synthesis method of Imatinib is disclosed, which comprises the following steps: the Imatinib, namely 4-(4-methyl-piperazin-1-ylmethyl)-N-[4-methyl-3-[4-(3-pyridinyl)-pyrimidin-2-ylamino]-benzamide shown in formula (III), is formed by reacting 4-methyl-N-3-(4-pyridin-3-yl-pyrimidin-2-yl)-1,3-benzenediamine shown in formula (I) with 4-(4-methyl-piperazin-1-methyl)-benzoic ester shown in formula (II), under the action of a base and in a non-protonic organic solvent,

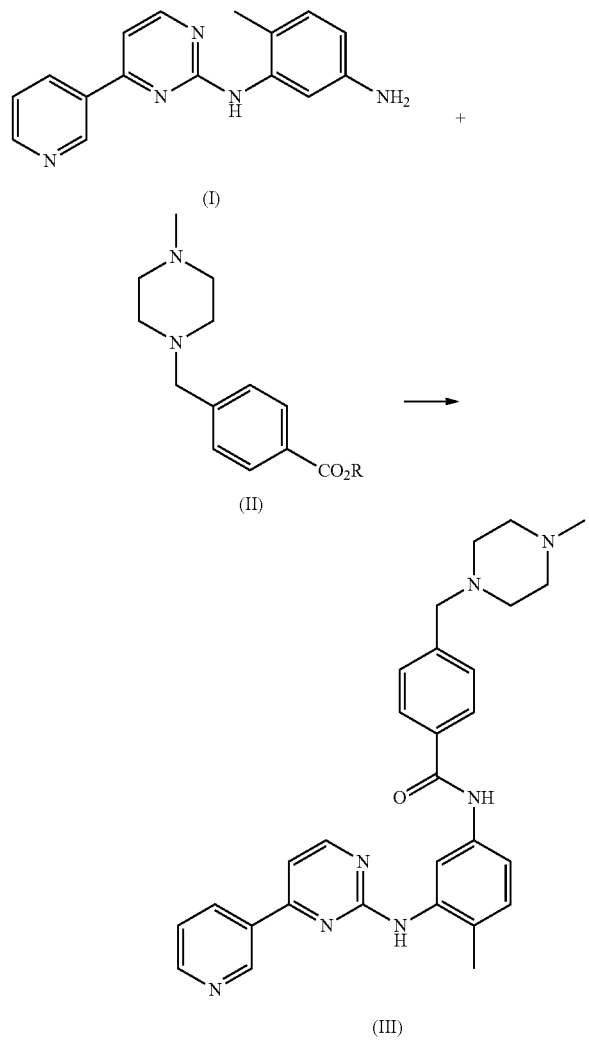

in the above generic chemical structural formula, R represents aliphatic alkyl having 1-10 carbon, phenyl, substituted phenyl, benzyl or substituted benzyl. The present invention provides a new synthesis method of Imatinib, which is formed under mild reaction conditions, and is environmentally friendly with a high-yield.

8 Claims, No Drawings

METHOD FOR SYNTHESIZING IMATINIB

TECHNICAL FIELD

The present invention relates to the field of organic synthesis, and in particular, to a synthesis method of Imatinib.

BACKGROUND OF THE INVENTION

Imatinib mesylate, which is a signal transduction inhibitor (i.e. the original STI571) developed by Novartis through seven years' efforts, is the first approved inhibitor of caner's signal transduction in the world. Imatinib mesylate has achieved the Orphan Drug Status in the U.S., EU and Japan, and was approved by the USFDA on May 10, 2001, for treating chronic myelogenous leukemia patients during the blast crisis phase, the accelerated phase and the choric phase for the failure of interfer on-alfa treatment.

The chemical name of Imatinib is 4-(4-methyl-piperazin-1-ylmethyl)-N-[4-methyl-3-[4-(3-pyridinyl)-pyrimidin-2-ylamino]-benzamide, and its structure is as follows:

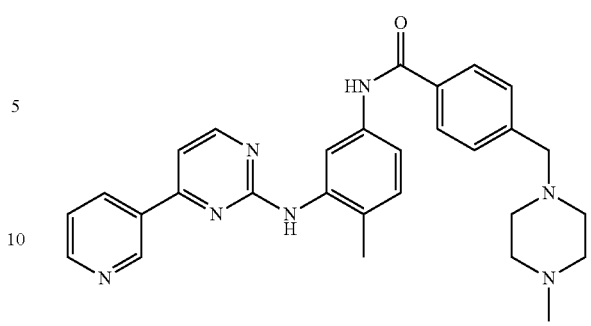

There are two major routes for synthesizing Imatinib on industrial scale. In route 1, Imatinib is prepared with 2-methyl-5-nitro-phenylamine as the starting material, by reacting it with cyanamide to form guanidine, then carrying out the cyclization with 3-dimethylamino-1-(3-pyridinyl)-2-propylene-1-ketone, further reducing the nitro group to amino, and followed by the condensation with p-chloromethyl-benzoyl chloride and N-methyl-piperazine sequentially (see WO 2004/108699).

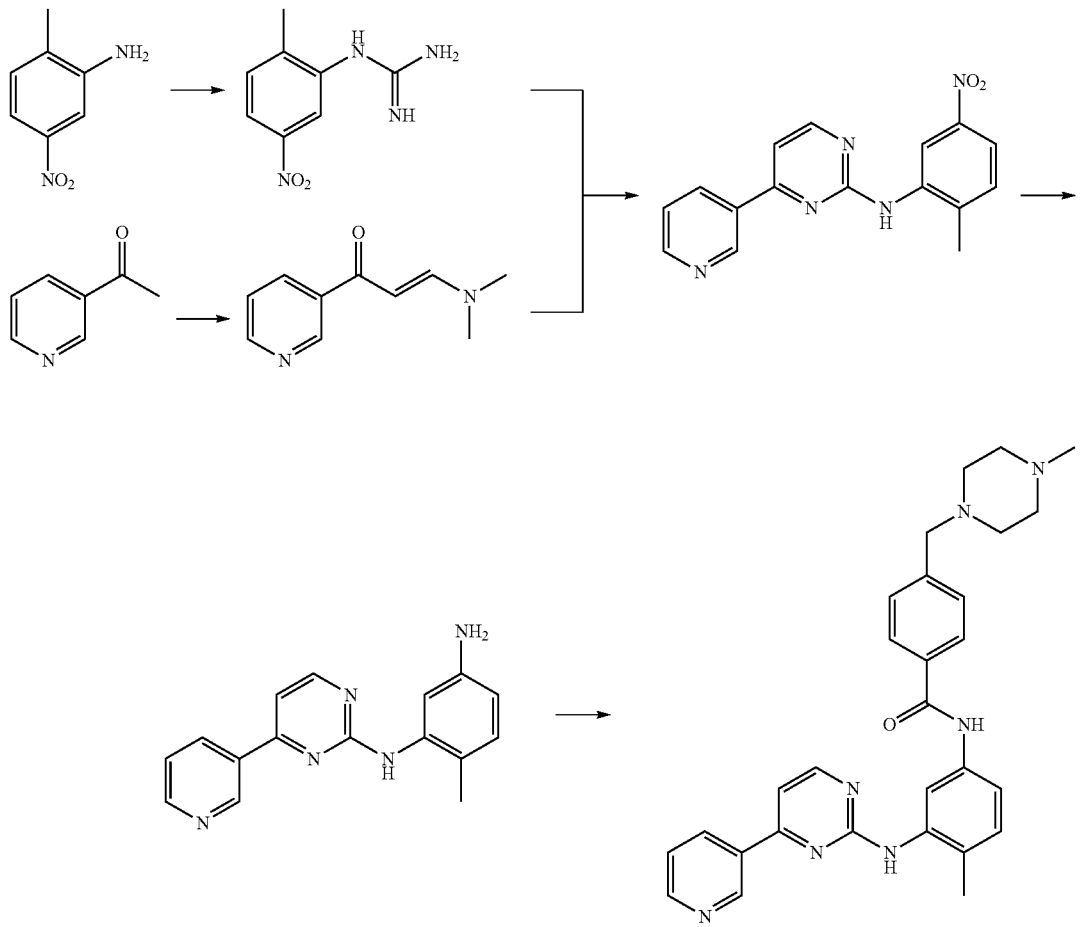

In route 2, Imatinib is prepared with 4-methyl-3-nitrophenylamine as starting material by sequentially carrying out the condensation with p-chloromethyl-benzoyl chloride and N-methyl-piperazine, then reducing the nitro group to amino, reacting with cyanamide to obtain guanidine, and followed by the cyclization with 3-dimethylamino-1-(3-pyridinyl)-2-propylene-1-ketone (WO 03/066613).

4-(4-methyl-piperazin-1-ylmethyl)-benzoic acid methyl ester with trimethylaluminium to obtain N-(4-methyl-3-bromo-phenyl)-4-(4-methyl-piperazin-1-ylmethyl)-benzamide, and finally reacting it with pyrimithamine under the catalysis of noble metal palladium. The disadvantages of this method include: 1) trimethylaluminium used in it is an inflammable chemical and will react violently with water; 2)

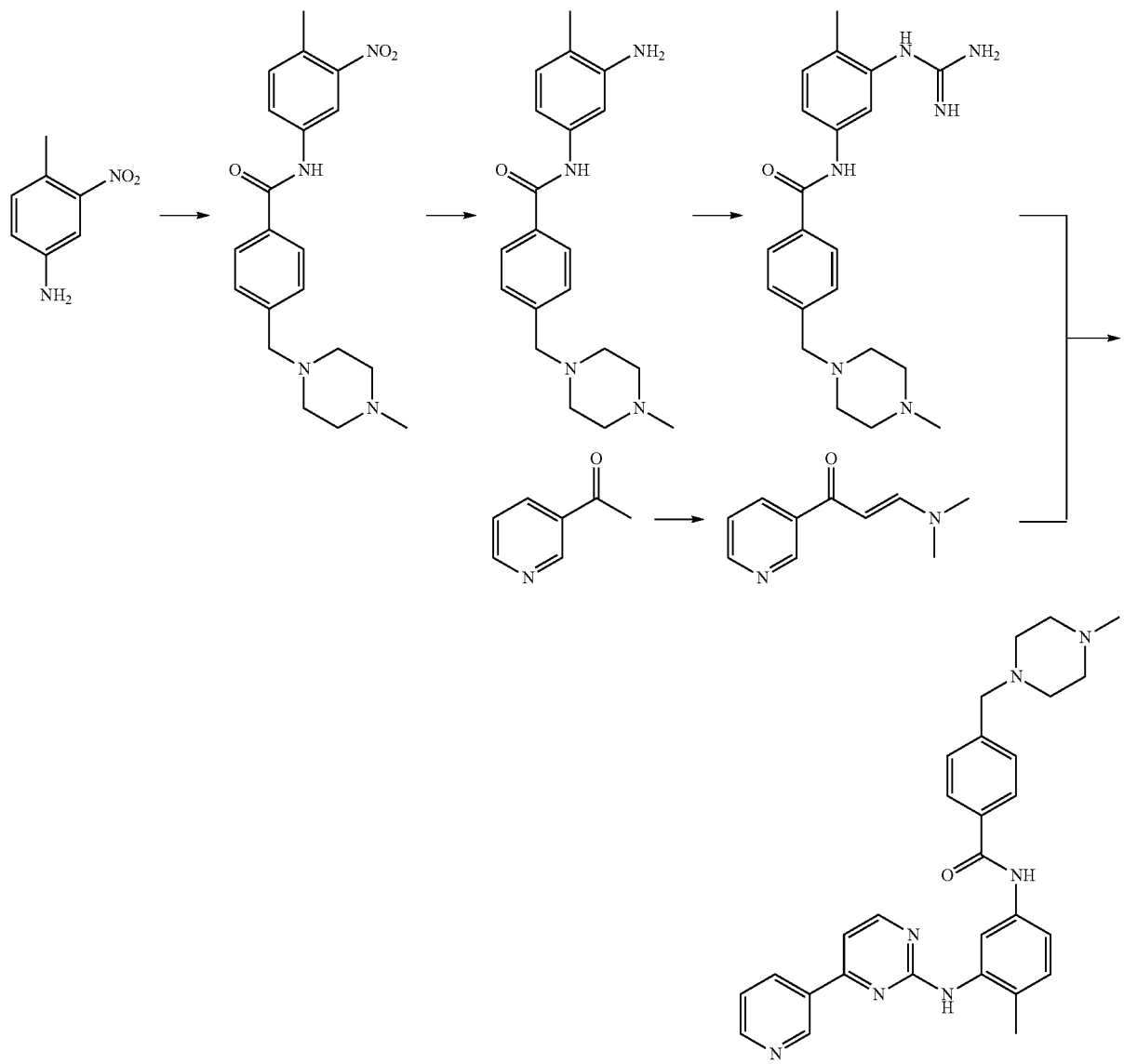

The major difference between these two routes lies in the sequence of cyclization of pyrimidine ring. However, both two routes have such disadvantages as: 1) the yield of guanidine is low and the guanidine thus obtained is unstable because it is synthesized by using cyanamide which has a low-boiling point and is volatile; 2) the synthesis of pyrimidine ring has a low-yield and takes long time, and the reaction of the raw material is incomplete.

Another method for synthesizing Imatinib is also disclosed in Chinese Patent No. CN1630648A. In that method, 3-bromo-4-methyl-phenylamine is used as raw material, Imatinib is obtained by carrying out the aminolysis reaction of the final product contains 10% isomers which are difficult to be purified.

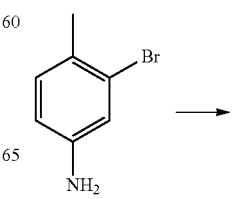

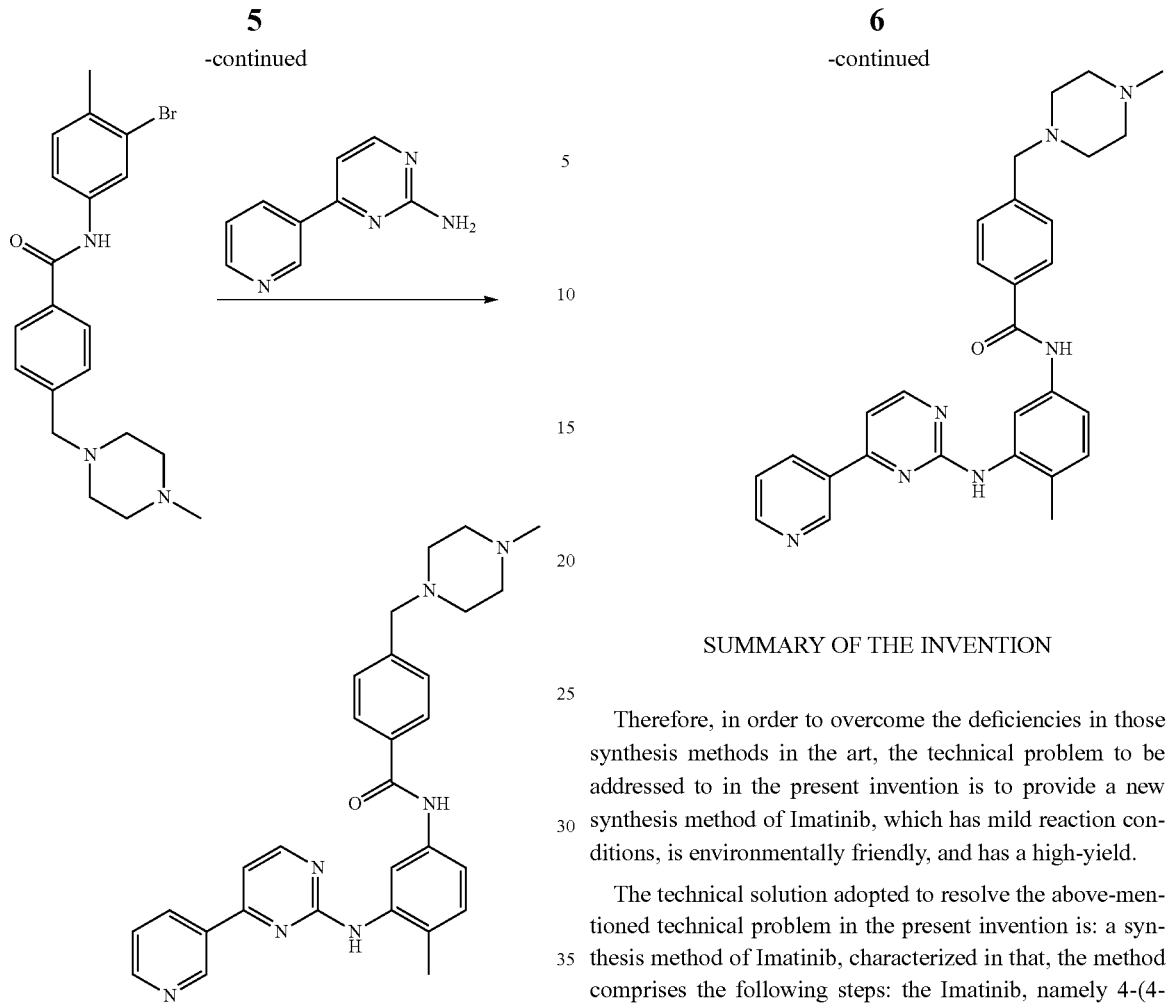

Another method for synthesizing Imatinib is disclosed in Chinese Patent No. CN101016293A. In that method, N-(4-methyl-3-3-amino-phenyl)-4-(4-methyl-piperazin-1-ylmethyl)-benzamide is the raw material and reacted with 2-halogeno-4-methyl-(3-pyridin-3-yl)-pyrimidine. The halogenated reagents used to synthesize 2-halogeno-4-methyl-(3-pyridin-3-yl)-pyrimidine, such as phosphorus oxychloride, are highly toxic, and have a serious influence on environmental.

SUMMARY OF THE INVENTION

Therefore, in order to overcome the deficiencies in those synthesis methods in the art, the technical problem to be addressed to in the present invention is to provide a new synthesis method of Imatinib, which has mild reaction conditions, is environmentally friendly, and has a high-yield.

The technical solution adopted to resolve the above-mentioned technical problem in the present invention is: a synthesis method of Imatinib, characterized in that, the method comprises the following steps: the Imatinib, namely 4-(4-methyl-piperazin-1-ylmethyl)-N-[4-methyl-3-[4-(3-pyridinyl)-pyrimidin-2-ylamino]-benzamide shown in formula (III), is formed by reacting 4-methyl-N-3-(4-pyridin-3-yl-pyrimidin-2-yl)-1,3-benzenediamine shown in formula (I) with 4-(4-methyl-piperazin-1-methyl)-benzoic acid ester shown in formula (II), under the action of a base and in an organic solvent:

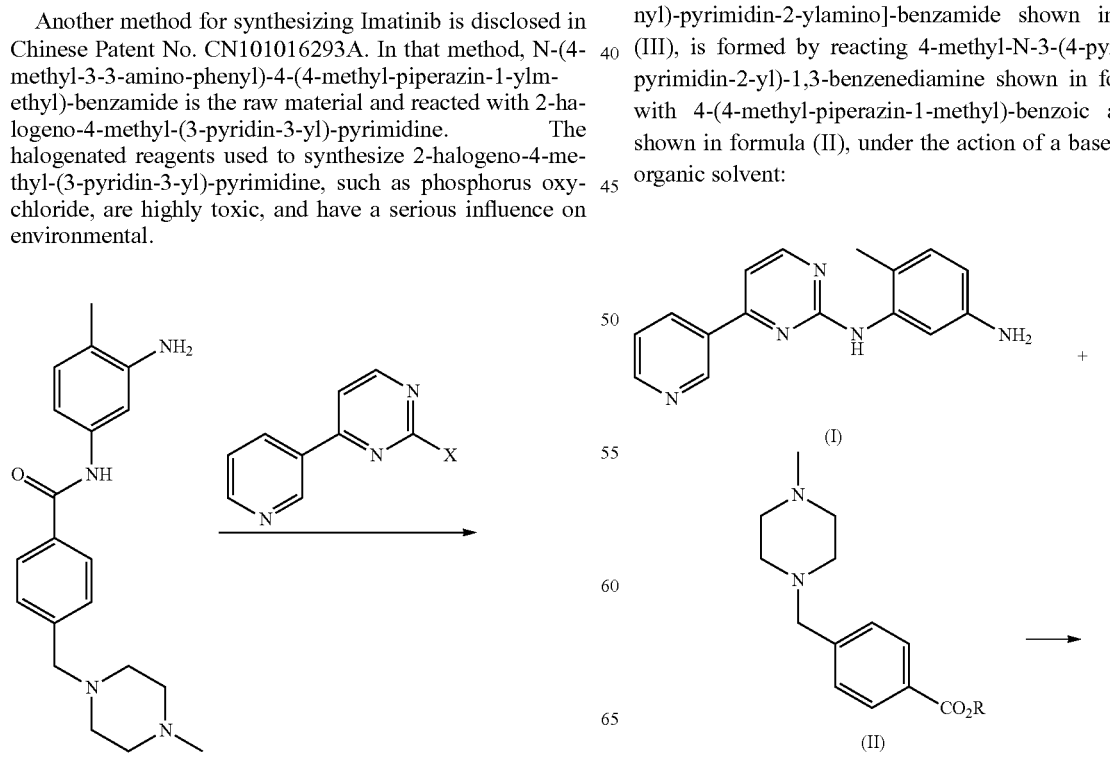

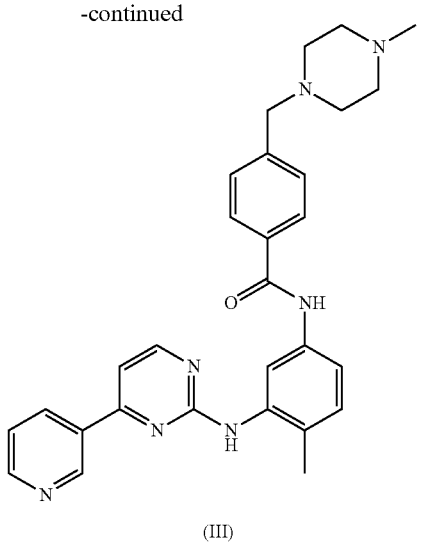

(III)

In the generic chemical structures shown above, R represents an aliphatic alkyl having 1-10 carbon, phenyl, substituted phenyl, benzyl or substituted benzyl.

In the present invention, the aliphatic alkyl having 1-10 carbon is preferably methyl, ethyl or propyl, the substituted phenyl is preferably p-methoxy-phenyl, and the substituted benzyl is preferably p-methoxy-benzyl.

In the present invention, the base can be an organic base or an inorganic bases. The organic base is one or more selected from sodium alcoholate, potassium alcoholate, butyl lithium, iso-butyl lithium, tert-butyl lithium, sodium hydroxide, potassium hydroxide, lithium hydroxide, cesium hydroxide and potassium carbonate. Herein, the sodium alcoholate is preferably selected from sodium methoxide, sodium ethoxide, sodium propoxide, sodium butoxide, sodium tert-butoxide and sodium benzoxide. The potassium alcoholate is preferably selected from potassium methoxide, potassium ethoxide, potassium propoxide, potassium butoxide, potassium tert-butoxide and potassium benzoxide. Preferably, the concentration of the base is 0.1-10 M, and more preferably, 1-2 M.

In the present invention, the organic solvent is preferably one or more selected from tetrahydrofuran, ether, dichloromethane, 1,2-dichloroethane, acetonitrile, alcohol of 1-4 carbon, toluene, ethyl acetate, dimethyl formamide, dimethyl sulfoxide and dimethylbenzene.

In the present invention, the reaction molar ratio of the compound shown in formula (I) to the compound shown in formula (II) is preferably 1:1 to 1:10, and most preferably 1:1.5 to 1:4. The amount of the organic solvent used is a regular amount in organic synthesis reactions.

In the present invention, the reaction temperature is preferably 0-100° C., and more preferably 25-50° C. The reaction continues until no reduction of the raw materials is detected.

The synthesis method of the compound shown in formula (I) can be learned from from WO 2004/108699:

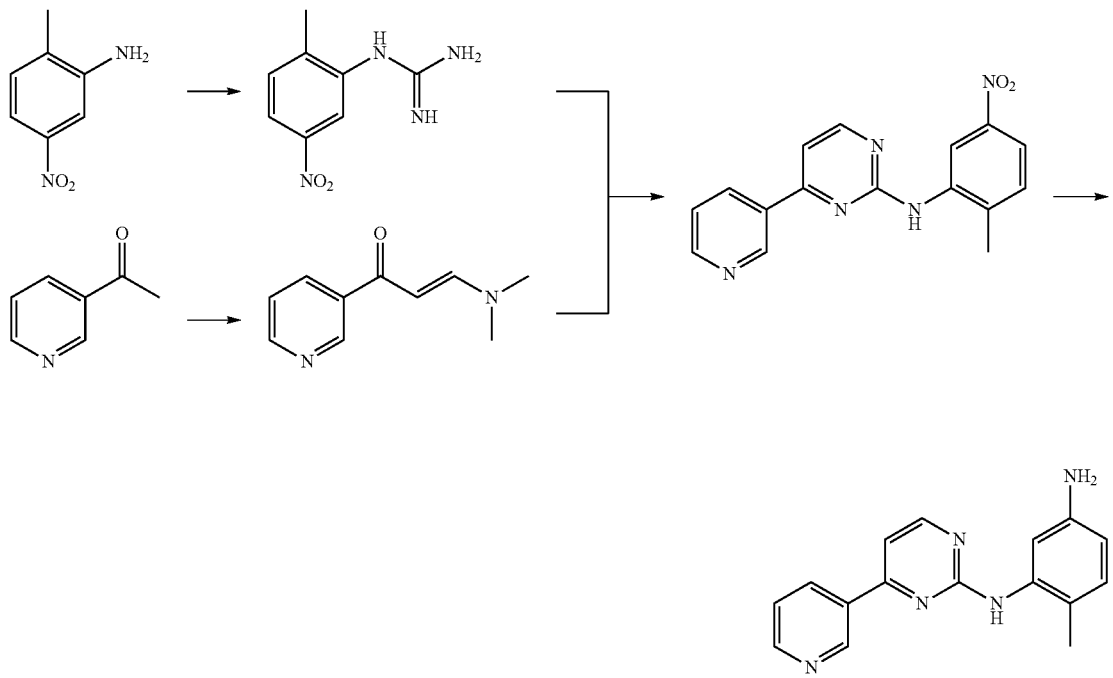

N-(2-methyl-5-nitro-phenyl)-guanidine is formed by the reaction of 2-methyl-5-nitro-phenylamine and cyanamide; pyrimidine compounds is obtained by reacting N-(2-methyl-5-nitro-phenyl)-guanidine reacted with 3-dimethylamino-1-pyridin-3-yl-propenone; and then the compound shown in formula (I) is obtained by reducing the nitro group.

The synthesis method of the compound shown in formula (II) can be learned in the Syn. Comm. 2003, 3597, which comprises the following steps: the sulphonic acid ester of p-halomethyl-benzonitrile or p-hydroxymethyl-benzonitrile is reacted with methylpiperazine, and then the cyano group is hydrolyzed to acid, and finally the acid is reacted with the corresponding alcohol to form the corresponding ester, i.e., the compound shown in formula (II);

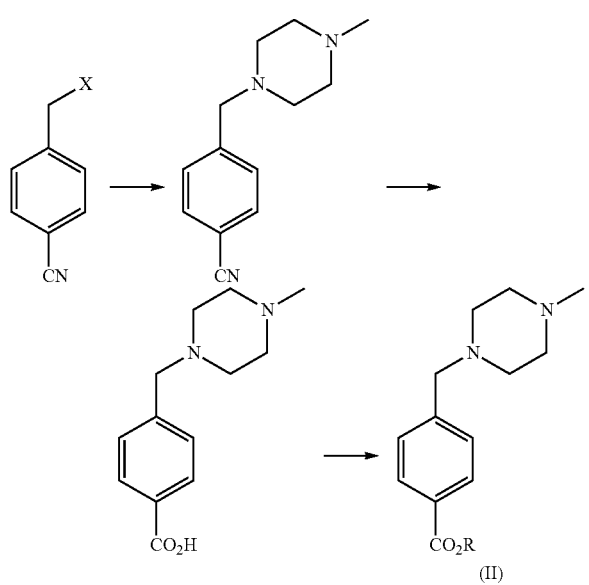

In the structural formula above, R represents an aliphatic alkyl having 1-10 carbon, phenyl, substituted phenyl, benzyl or substituted benzyl; and X represents Cl, Br, I, OMs or OTs.

The raw materials or reagents used in the present invention are commercially available, unless specified otherwise.

Compared to the prior art, the beneficial effects of the present invention inlcude:
1. In the method of the present invention, the product yield is significantly increased because the aminolysis of ester is complete.
2. In the method of the present invention, the by-product of the aminolysis is the corresponding alcohol, which is environmentally friendly.
3. In the method of the present invention, the reaction conditions are mild, the reaction is easily operated, and is suitable for industrialized production.

DETAILED DESCRIPTION OF THE INVENTION

In combination with the embodiments, the present invention will be further described as follows, but the present invention is not to be limited by these embodiments. In the following embodiments, the experimental methods without giving specified conditions were usually carried out under the regular conditions or under the conditions advised by the manufacturer.

Embodiment 1

In a 500 ml dried 4-neck flask, 250 ml tetrahydrofuran,27.7 g 4-methyl-N-3-(4-pyridin-3-yl-pyrimidin-2-yl)-1,3-benzenediamine, and 25 g 4-(4-methyl-piperazin-1-methyl)-benzoic acid methyl ester were added. After it was stirred to dissolve, 10 g sodium methoxide was then added. The mixture was heated to 70° C. for reflux and reaction overnight until the reaction was detected to be complete, and then was concentrated to remove tetrahydrofuran. The residue solid was washed with water and dried, thus 45 g Imatinib was obtained, and the yield was 91.0%.

The data of spectrum is as follows: $^1$H NMR (500M, DMSO) δ:10.2 (s, 1H), 9.30 (s, 1H), 8.99 (s, 1H), 8.72 (d, J=4.0 Hz, 1H), 8.57 (s, 1H), 8.53 (s, 1H), 8.11 (s, 1H), 8.00 (s, 1H), 7.98 (s, 1H), 7.58-7.51 (m, 4H), 7.44 (d, J=4.3 Hz, 1H), 7.22 (d, J=8.1 Hz, 1H), 3.70 (s, 2H), 3.50-3.25 (m, 2H), 3.20-2.90 (m, 4H), 2.81 (s, 3H), 2.40 (s, 3H), 2.24 (s, 3H). $^{13}$C NMR (125M, DMSO) δ:164.9, 161.3, 161.1, 159.4, 150.8, 147.7, 137.7, 137.1, 134.9, 134.3, 132.3, 129.9, 129.1, 127.7, 127.6, 123.9, 117.2, 116.8, 107.5, 59.9, 52.1, 48.9, 42.2, 17.5. MS (M$^+$+1):494.3

Embodiment 2

In a 5000 ml dried 4-neck flask, 3000 ml dichloromethane, 277 g 4-methyl-N-3-(4-pyridin-3-yl-pyrimidin-2-yl)-1,3-benzenediamine, and 270 g 4-(4-methyl-piperazin-1-methyl)-benzoic acid ethyl ester were added. After it was stirred to dissolve, 100 g sodium methoxide was then added. The mixture was heated to 40° C. for reflux and reaction overnight until the reaction was detected to be complete, and then was concentrated to remove toluene. The residue solid was washed with water and dried, thus 455 g Imatinib was obtained, and the yield was 92.0%. The data of spectrum is the same as above.

Embodiment 3

In a 5000 ml dried 4-neck flask, 3000 ml toluene,277 g 4-methyl-N-3-(4-pyridin-3-yl-pyrimidin-2-yl)-1,3-benzenediamine, and 450 g 4-(4-methyl-piperazin-1-methyl)-benzoic acid benzyl ester were added. After it was stirred to dissolve, 200 g sodium ethoxide was then added. The mixture was heated to 50° C. for reaction overnight until the reaction was detected to be complete, and then concentrated to remove toluene. The residue solid was washed with water and dried, thus 445 g Imatinib was obtained, and the yield was 90.0%. The data of spectrum is the same as above.

Embodiment 4

In a 50 L reaction kettle, 25 L dimethyl formamide,2.77 kg 4-methyl-N-3-(4-pyridin-3-yl-pyrimidin-2-yl)-1,3-benzenediamine, and 3.50 kg 4-(4-methyl-piperazin-1-methyl)-benzoic acid propyl ester were added. After it was stirred to dissolve, 3 kg potassium butoxide was then added. The mixture was heated to 50° C. for reaction overnight until the reaction was detected to be complete, and then was poured into water to separate out the solid. The residue solid was centrifuged, then washed with water and dried, thus 4.45 kg Imatinib was obtained, and the yield was 90.0%. The data of spectrum is the same as above.

Embodiment 5

In a 5000 mL dried 4-neck flask, 3000 ml acetonitrile, 277 g 4-methyl-N-3-(4-pyridin-3-yl-pyrimidin-2-yl)-1,3-benzenediamine, and 450 g 4-(4-methyl-piperazin-1-methyl)-benzoic acid 4-methoxy-benzyl ester were added. After it was stirred to dissolve, 400 mL (2.5M) butyl lithium was then added. The mixture was heated to 20° C. for reaction overnight until the reaction was detected to be complete, and then concentrated to remove acetonitrile. The obtained solid was washed with water and dried, thus 445 g Imatinib was obtained, and the yield is 90.0%. The data of spectrum is the same as above.

Embodiment 6

In a 5000 mL dried 4-neck flask, 3000 mL propanol, 277 g 4-methyl-N-3-(4-pyridin-3-yl-pyrimidin-2-yl)-1,3-benzenediamine, and 2250 g 4-(4-methyl-piperazin-1-methyl)-benzoic acid phenyl ester were added. After it was stirred to dissolve, 1500 g cesium hydroxide was then added. The mixture was heated to 80° C. for reaction overnight until the reaction was detected to be complete, and then concentrated to remove propanol. The obtained solid was washed with water and dried, thus 450 g Imatinib was obtained, and the yield is 90.5%. The data of spectrum is the same as above.

Embodiment 7

In a 5000 ml dried 4-neck flask, 3000 ml ethyl acetate, 277 g 4-methyl-N-3-(4-pyridin-3-yl-pyrimidin-2-yl)-1,3-benzenediamine, and 450 g 4-(4-methyl-piperazin-1-methyl)-benzoic acid p-tolyl ester were added. After it was stirred to dissolve, 138 g potassium carbonate was then added. The mixture was heated 50° C. for reaction overnight until the reaction was detected to be complete and concentrated to remove ethyl acetate. The obtained solid was washed with water and dried, thus 445 g Imatinib was obtained, and the yield is 90.0%. The data of spectrum is the same as above.

Embodiment 8

In a 5000 mL dried 4-neck flask, 3000 ml dimethyl sulfoxide, 277 g 4-methyl-N-3-(4-pyridin-3-yl-pyrimidin-2-yl)-1, 3-benzenediamine, and 450 g 4-(4-methyl-piperazin-1-methyl)-benzoic acid p-tolyl ester were added. After it was stirred to dissolve, 800 g sodium hydroxide was then added. The mixture was heated to 70° C. for reaction overnight until the reaction was detected to be complete and then concentrated to remove dimethyl sulfoxide. The obtained solid was washed with water and dried, thus 445 g Imatinib was obtained, and the yield was 90.0%. The data of spectrum is the same as above.

Embodiment 9

In a 5000 mL dried 4-neck flask, 3000 ml ether, 277 g 4-methyl-N-3-(4-pyridin-3-yl-pyrimidin-2-yl)-1,3-benzenediamine, and 1500 g 4-(4-methyl-piperazin-1-methyl)-benzoic acid benzyl ester were added. After it was stirred to dissolve, 1000 g (1 mol) sodium benzoxide was then added. The mixture was cooled to 0° C. for reaction overnight until the reaction was detected to be complete and then concentrated to remove ether. The obtained solid was washed with water and dried, thus 445 g Imatinib was obtained, and the yield was 90.0%. The data of spectrum is the same as the above.

What is claimed is:

1. A method for synthesizing Imatinib, characterized in that, the method comprises the following steps: 4-(4-methyl-piperazin-1-ylmethyl)-N-[4-methyl-3-[4-(3-pyridinyl)-pyrimidin-2-ylamino]-benzamide shown in formula (III), is formed by reacting 4-methyl-N-3-(4-pyridin-3-yl-pyrimidin-2-yl)-1,3-benzenediamine shown in formula (I) with 4-(4-methyl-piperazin-1-methyl)-benzoic ester shown in formula (II), under the action of a base and in an organic solvent,

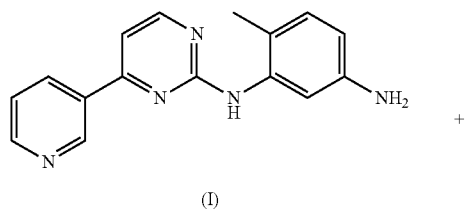

(I)

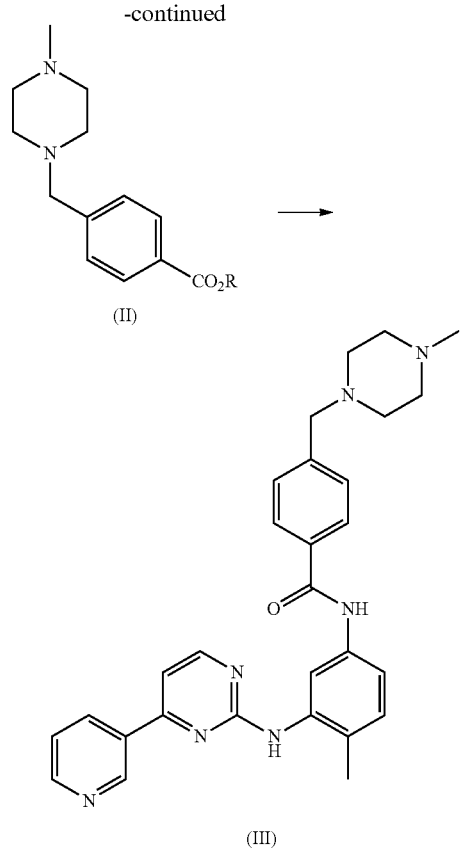

in the above generic chemical structural formula, R represents an aliphatic alkyl having 1-10 carbon, phenyl, substituted phenyl, benzyl or substituted benzyl.

2. The synthesis method according to claim 1, characterized in that the aliphatic alkyl having 1-10 carbon is methyl, ethyl or propyl, the substituted phenyl is p-methyl-phenyl, and the substituted benzyl is p-methoxy-benzyl.

3. The synthesis method according to claim 1, characterized in that the reaction molar ratio of the compound shown in formula (I) to the compound shown in formula (II) is 1:1 to 1:5.

4. The synthesis method according to claim 1, characterized in that the base is one or more selected from sodium alcoholate, potassium alcoholate, butyl lithium, iso-butyl lithium, tert-butyl lithium, sodium hydroxide, potassium hydroxide, lithium hydroxide, cesium hydroxide and potassium carbonate.

5. The synthesis method according to claim 1, characterized in that the concentration of the base is 0.1-10 M.

6. The synthesis method according to claim 1, characterized in that the organic solvent is one or more selected from tetrahydrofuran, ether, dichloromethane, 1,2-dichloroethane, acetonitrile, alcohol of 1-4 carbon, toluene, ethyl acetate, dimethyl formamide, dimethyl sulfoxide and dimethylbenzene.

7. The synthesis method according to claim 1, characterized in that reaction temperature is 0-80° C.

8. The synthesis method according to claim 1, characterized in that the reaction continues until no raw materials of reaction is detected.

* * * * *